(12) United States Patent
Strömberg (10) Patent No.: US 7,040,315 B1
(45) Date of Patent: May 9, 2006

(54) ARRANGEMENT FOR ANAESTHETISING A LIVING CREATURE

(75) Inventor: Stefan Strömberg, Sigtuna (SE)

(73) Assignee: Aneo AB, Marsta (SE)

( * ) Notice: Subject to any disclaimer, the term of this patent is extended or adjusted under 35 U.S.C. 154(b) by 0 days.

(21) Appl. No.: 09/959,841

(22) PCT Filed: May 8, 2000

(86) PCT No.: PCT/SE00/00910

§ 371 (c)(1),
(2), (4) Date: Feb. 4, 2002

(87) PCT Pub. No.: WO00/67820

PCT Pub. Date: Nov. 16, 2000

(30) Foreign Application Priority Data

May 10, 1999 (SE) .................................. 9901688

(51) Int. Cl.
*A61M 15/00* (2006.01)
*A61M 16/00* (2006.01)
(52) U.S. Cl. ..................... 128/203.14; 128/203.13; 128/204.18; 128/204.22
(58) Field of Classification Search .......... 128/203.12, 128/203.13, 203.14, 203.26, 203.27, 203.28, 128/204.18, 204.22
See application file for complete search history.

(56) References Cited

U.S. PATENT DOCUMENTS

| 4,452,241 | A | * | 6/1984 | Sarnoff et al. ......... 128/204.18 |
| 4,589,409 | A | * | 5/1986 | Chatburn et al. ....... 128/203.26 |
| 5,007,688 | A | | 4/1991 | Bayerlein et al. |
| 5,072,726 | A | * | 12/1991 | Mazloomdoost et al. ..................... 128/200.14 |
| 5,101,820 | A | * | 4/1992 | Christopher ........... 128/204.18 |
| 5,188,098 | A | * | 2/1993 | Hoffman et al. ....... 128/204.23 |
| 5,320,093 | A | * | 6/1994 | Raemer .................. 128/203.12 |
| 5,355,872 | A | * | 10/1994 | Riggs et al. ........... 128/200.21 |
| 5,547,470 | A | * | 8/1996 | Johnson et al. ............... 604/67 |
| 5,590,648 | A | * | 1/1997 | Mitchell et al. ............ 600/301 |
| 5,722,392 | A | * | 3/1998 | Skimming et al. ..... 128/203.12 |
| 5,735,268 | A | * | 4/1998 | Chua et al. ............ 128/204.23 |
| 5,873,361 | A | * | 2/1999 | Hakala .................. 128/204.23 |
| 5,902,253 | A | * | 5/1999 | Pfeiffer et al. .............. 600/584 |
| 5,918,596 | A | * | 7/1999 | Heinonen .............. 128/204.21 |
| 6,010,118 | A | * | 1/2000 | Milewicz ..................... 261/142 |
| 6,085,743 | A | * | 7/2000 | Rosen et al. ........... 128/200.24 |
| 6,089,105 | A | * | 7/2000 | Ricciardelli .............. 73/861.52 |
| 6,131,571 | A | * | 10/2000 | Lampotang et al. ... 128/204.21 |
| 6,138,668 | A | * | 10/2000 | Patton et al. .......... 128/200.14 |
| 6,186,977 | B1 | * | 2/2001 | Andrews et al. .............. 604/67 |

(Continued)

*Primary Examiner*—Glenn K. Dawson
*Assistant Examiner*—Michael G Mendoza
(74) *Attorney, Agent, or Firm*—Banner & Witcoff, Ltd.

(57) ABSTRACT

The invention relates to an arrangement (200) for anaesthetising a living creature (V) and for maintaining said creature in an anaesthetised state, by administering thereto an infused volume of anaesthesia inducing pharmaceutical (22) in liquid phase per unit of time, with the aid of one or more lung ventilator units (A) and one or more infusion units (B). Chosen parts of the lung ventilator unit, with the exception of external insufflation hose, expiration valve, measuring probe and a number of hoses (12), and selected parts of the infusion unit (B), with the exception of cannula (5B) and hose (4B) are mutually combined to form a single equipment unit (201). Some of the parts of the equipment unit are mutually coordinated with respect to communication via a computer unit (600) included in the equipment unit, and the computer unit is adapted to monitor unit related criteria and creature related criteria.

12 Claims, 6 Drawing Sheets

U.S. PATENT DOCUMENTS

| | | | |
|---|---|---|---|
| 6,193,655 B1 * | 2/2001 | McGrath | 600/301 |
| 6,234,172 B1 * | 5/2001 | Ausbourne et al. | 128/845 |
| 6,237,597 B1 * | 5/2001 | Kovac | 128/207.14 |
| 6,240,920 B1 * | 6/2001 | Strom | 128/204.23 |
| 6,253,765 B1 * | 7/2001 | Hognelid et al. | 128/204.18 |
| 6,272,933 B1 * | 8/2001 | Gradon et al. | 73/861 |
| 6,279,576 B1 * | 8/2001 | Lambert | 128/205.28 |
| 6,647,984 B1 * | 11/2003 | O'Dea | 128/207.16 |
| 6,648,832 B1 * | 11/2003 | Orr et al. | 600/532 |
| 6,709,405 B1 * | 3/2004 | Jonson | 600/538 |
| 6,837,241 B1 * | 1/2005 | Samzelius | 128/204.21 |
| 6,851,426 B1 * | 2/2005 | Stromberg | 128/204.21 |

* cited by examiner

ARRANGEMENT FOR ANAESTHETISING A LIVING CREATURE

This is a U.S. National Phase Application Under 35 USC 371 and applicant herewith claims the benefit of priority of PCT/SE00/00910 filed May 8, 2000, which was published Under PCT Article 21(2) in English and Application No. 9901688-3 filed in Sweden on May 10, 1999.

FIELD OF INVENTION

The present invention relates to an arrangement for initially anaesthetising a living creature and to keep the creature within adapted levels of said anaesthetic state, the so-called depth of anaesthesia.

Such states and depths of anaesthesia are achieved by infusing or injecting into a living creature a volume of anaesthesia inducing pharmaceutical in a liquid phase per unit of time.

By "infused" is meant the continuous or intermittent and/or controllable delivery of said pharmaceutical (anaesthetic) to a blood-carrying vessel, preferably intravenously.

During this state there is required, among other things, the use of a lung ventilator and associated control unit, and an infusion unit and associated control unit, to regulate the increase in or reduction in the volume of pharmaceutical per unit of time required to regulate the depth of anaesthesia.

In addition, arrangements of this kind comprise and/or include a plurality of sensors and/or measuring probes adapted to sense selected creature-associated criteria and to produce a signal that corresponds to the chosen criterion and its value or intensity at that moment in time.

Examples of criteria thus selected and their intensity will be mentioned in the following text.

The invention can be applied to any living creature that has a lung function and will be illustrated in the following with reference to its application on a human being, represented by a patient undergoing surgery, by way of simplification.

DESCRIPTION OF THE BACKGROUND ART

With respect to earlier known apparatus and arrangements for anaesthetising a patient to a chosen depth of anaesthesia, it is normal to divide such states into three different categories, depending on the degree of consciousness of the patient, namely:

general anaesthesia, a state in which the patient is rendered unconscious artificially and kept within adapted degrees or levels of unconsciousness (depth of anaesthesia);

regional anaesthesia, a state of insensitivity in the spine of a patient; and local anaesthesia a state which is mainly applicable to minor surgery or treatment.

The patients are conscious in the latter two categories.

The present invention is adapted for application in the general anaesthesia category.

This category includes two different groups of anaesthesia, namely inhalation anaesthesia and total intravenous anaesthesia.

There is used within the first anaesthesia group, inhalation anaesthesia, a lung ventilator that includes vaporiser equipment for anaesthesia inducing pharmaceutical, said lung ventilator creating conditions for the insufflation and expiration of air or air mixed with gaseous oxygen, which is mixed, in turn with anaesthesia inducing gases.

Although apparatus designed for inhalation anaesthesia have found wide use, they require the appropriation of very complicated equipment, partly to enable the insufflation and expiration phases to be controlled and partly to administer the supply of gaseous pharmaceutical, and also to evaluate patient related criteria and to regulate said criteria when necessary.

Thus, it is likely that anaesthesia inducing gases will accompany the expiration gas in each expiration phase and consequently it is necessary to remove these gases from every enclosed space, such as the operating theatre, effectively and at short intervals. In addition, the equipment must, of course, be gas tight in general.

It is also known in the case of such practice to assemble an inhalation anaesthesia related system within respective clinics with the aid of different apparatus obtained from different manufacturers and designed for different purposes.

It is also known to appropriate a single system from a single manufacturer. Such systems, however, are highly complicated and the component parts of such systems make the equipment extremely heavy. It is also found that such a system is space consuming and expensive and that the necessary inspections for possible leakage are very difficult to carry out.

The present invention relates to and includes an arrangement within the second anaesthesia group, i.e. total intravenous anaesthesia, wherein a volume of occurring or existing anaesthesia-inducing pharmaceutical in liquid phase is allowed to infuse per unit of time into the bloodstream of the living creature or patient.

It is necessary in this case to use a lung ventilator and an infusion unit which, with the aid of a control unit, is able to induce a given depth of anaesthesia in the patient and to keep the patient within adapted levels of said chosen depth of anaesthesia.

It is known in this respect to use a number of apparatus taken from different manufacturers and to assemble these apparatus into a system or an arrangement. In order to induce a given depth of anaesthesia in a patient, each such system requires the use of a number of apparatus and measuring devices which function to enable a number of important patient criteria to be evaluated and to enable the well-being of the patient to be controlled. These criteria have normally been presented as instantaneous values and/or curves on the display surface of each apparatus.

Criteria that concern the well-keeping/treatment of a patient are designated therapeutic criteria and are detected/ sensed, regulated and evaluated in one or more therapeutic units.

Criteria that relate to patient diagnosis or patient supervision are referred to as diagnostic criteria and are sensed/ detected and evaluated in one or more diagnostic units.

Figure 1:
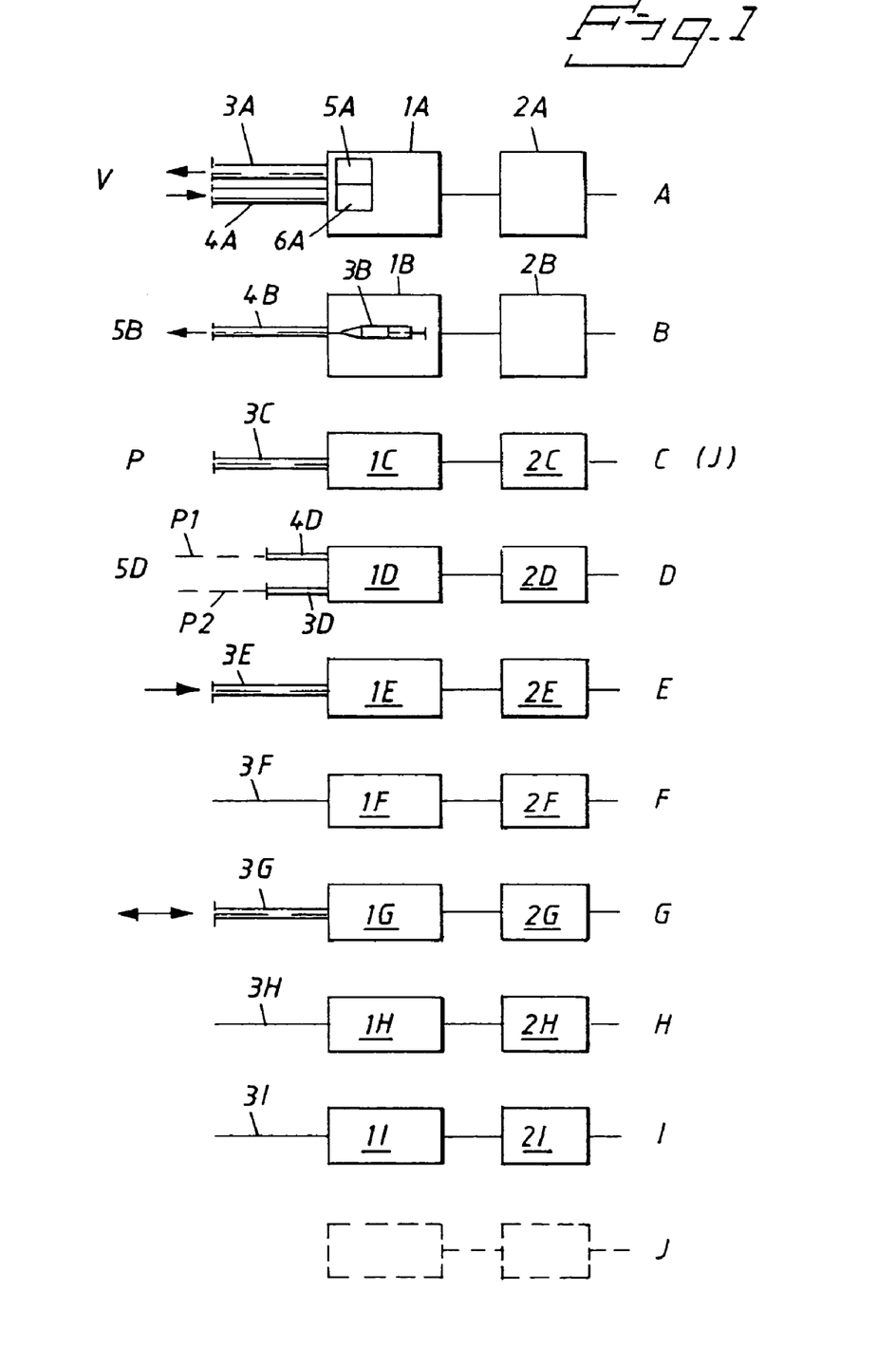

Some significant units and criteria in the present context have been listed in FIG. 1, in which reference sign A identifies a lung ventilator and an associated control unit; B identifies an infusion unit and associated control unit for making necessary adjustments to the volume of anaesthesia inducing pharmaceutical per unit of time; C identifies a unit which senses/detects prevailing air pressure, i.e. the air pressure in the mouth of the patient; D identifies a unit which evaluates the flow of air into the patient's lungs and, when necessary, also out of the lungs; E identifies a unit which evaluates the $CO_2$-content and the $O_2$-content of the air entering the lungs, and when necessary also the expiration air; F identifies a unit for evaluating ECG-values; G identifies a unit that evaluates blood pressure values NIBP; H identifies a unit for establishing oxygen saturation in the blood ($SpO_2$); I identifies a unit which evaluates the degree of consciousness of the patient (the depth of anaesthesia) via sensed brain activity (the BIS-values); and J identifies a unit which evaluates PEEP-value.

It is known in systems of this nature adapted for total intravenous anaesthesia to allow a number of the criteria given under A–J above to be interconnected and combined in a common unit.

For instance, it is known to combine the units for criteria C and J and for A, D and E respectively into a single unit. The criterion B and combinations of criteria F, G and H normally require separately operated and individual units.

Known technology teaches the use of the infusion unit B and the lung ventilator A as separate units. These units are used to control the well-being of the patient and therefore include a number of therapeutic units.

Other equipment and units are primarily designed to produce instantaneous values or curves for other relevant patient-related criteria and include a number of diagnostic units.

By instantaneous values shall be understood measured values that can be evaluated instantaneously in the true meaning of the word, and also the formation of mean values of a selected number of sensed/detected instantaneous measurement values.

In the case of so-called multi-parameter monitors, it is known to co-ordinate the evaluated instantaneous values and the values for presentation of time-related graphs for selected relevant criteria and to show these graphs on a display surface.

SUMMARY OF THE PRESENT INVENTION

Technical Problems

When taking into consideration the technical deliberations that a person skilled in this particular art must make in order to provide a solution to one or more technical problems that he/she encounters, it will be seen that on the one hand it is necessary to realise the measures and/or the sequence of measures that must be undertaken to this end, and on the other to realise which means is/are required in solving one or more of said problems. On this basis, it will be evident that the technical problems listed below are highly relevant to the development of the present invention.

When considering the present standpoint of techniques as described above, it will be seen that a technical problem is one of providing with simple means an arrangement which enables the infusion of anaesthesia inducing pharmaceutical and which is based on principles for total intravenous anaesthesia while using one or more lung ventilator units and one or more infusion units, with first means for monitoring unit-related criteria, and second means for monitoring patient-related criteria, therewith creating conditions for a compact and mobile arrangement.

In this respect, a technical problem resides in realising the significance of and the advantages afforded by allowing the component parts of the chosen lung ventilator, with the exception of insufflation hose, expiration valve, measuring probe and a number of hoses, and the component parts of the infusion unit, with the exception of cannula and hose, to be combined into a single equipment unit, and to mutually co-ordinate certain of said equipment unit parts from the aspect of communication through the medium of a computer unit arranged in the equipment unit, and to program the computer unit to monitor patient related criteria and unit related criteria.

In addition, a technical problem resides in realising the significance of and the advantages that are associated with programming the computer unit to distinguish between therapeutic criteria and diagnostic criteria through the medium of therapeutic units and diagnostic units included and mounted in said equipment unit.

Another technical problem resides in realising the significance of and advantages afforded by structuring one or more therapeutic unit and/or one or more diagnostic units on a printed circuit board or card and, when applicable, function units mounted on or related to said circuit board, and coordinating several such boards in the equipment unit, wherewith an input of respective units is coupled internally in the equipment unit to one part of a two-part coupling means, where said parts are fastened to and co-ordinate in said equipment unit, and to realise that said parts of the coupling means belonging to said equipment unit shall be comprised of one or more hose couplings and one or more couplings/connections for electric conductors or cables.

It will also be seen that a technical problem resides in the provision of conditions with the aid of simple measures that enable an external insufflation-hose section for the lung ventilator unit and its coupling part associated with said equipment unit to be co-ordinated with further external hose parts so as to enable an external hose bundle or assembly to be used, said hose bundle conveniently including a hose for controlling a patient-proximal expiration valve, two hose parts for measuring pressure differences, a hose part for measuring pressure and/or a gas sampling hose part.

In addition, a technical problem resides in providing with the aid of simple measures conditions which allow the infusion unit to include a container that is held detachably by the equipment unit and that contains an anaesthesia inducing pharmaceutical in liquid phase.

Another technical problem is one of creating with the aid of simple measures conditions which enable the coupling parts associated with the equipment unit to be connected to a measuring probe, sensor or like device peripherally situated and separated from the equipment unit, through the medium of a hose part or an electric conductor, where said measuring probe, sensor or like device may include electronic circuits that are designed to sense the occurrence of patient related criteria and to establish the values of said criteria.

It will also be seen that a technical problem resides in providing with the aid of simple measures conditions that will enable such an equipment unit to be coupled to and/or readily releasably connected to a display unit adapted to display on a display surface one or more of the instantaneous values of criteria and/or timewise variation of said criterion.

In this respect, a technical problem resides in realising the significance of and the advantages that are afforded by presenting requisite diagnostic criteria and requisite therapeutic criteria in a co-ordinated fashion, thereby greatly assisting the anaesthetist and the surgeon in controlling and regulating the therapeutic criteria and/or diagnostic criteria of the patient, such as the depth of anaesthesia and/or other changeable states.

Another technical problem is one of creating with the aid of simple means or measures conditions which enable the timewise variation of a number of chosen criteria to be presented on an image screen or display surface with at least some chosen time axes coordinated, for instance superimposed with respect to each other, and, when necessary, compensating for any lag time in evaluating the measuring result.

Another technical problem is one of providing with the aid of simple measures conditions that allow the timewise variation of one or more, although only a few, chosen criteria to be presented on an image screen or display surface in a time-axes time scale that is different to the time axes for other criteria.

Another technical problem is one of realising the coordination that is required to allow the predominant part of requisite circuits, units and equipment to be combined into a single equipment unit, where requisite measuring points, measuring probes, sensors, etc. can be connected to said equipment unit via coupling means in an easy and functionally reliable fashion.

Another technical problem resides in providing an arrangement capable of readily effecting in the equipment unit such requisite processes as gas sampling/measuring, flow measuring, volume measuring, pressure measuring, ECG-measuring, saturation measuring and/or measuring the depth of anaesthesia.

Yet another technical problem is one of providing an arrangement of the kind described in the introduction in which the equipment unit used is adapted to include the major part of a lung ventilator and its associated control unit, and to couple said ventilator to a computer unit.

It will also be seen that a technical problem is one of realising the significance of providing an arrangement in which the entire lung ventilator is incorporated in the equipment unit, with the exception of a hose portion that conducts insufflation gas to the patient, an outer portion of said hose for connection to an expiration valve, one or more hose portions extending between said valve and said unit, a hose portion for actuation of the expiration valve to one of two positions from the equipment unit, a hose portion for determining gas pressure values and an adapted lowest overpressure value, and two hose portions belonging to the measuring probe for transferring flow-dependent gas pressure values to the equipment unit, said values being used to measure flow, and also said measuring probe and a hose portion for gas analysis.

It will also be seen that a technical problem resides in creating conditions which enable all important function units to be combined in one single equipment unit, so that said unit can be attached to a readily accessible first part of a two-part hose coupling, said coupling part being adapted for coaction with a number of further hoses in addition to coaction with an outer hose part for insufflation gas.

It will also be seen that in respect of an arrangement of the kind described in the introduction a technical problem resides in enabling readily available first coupling parts of one or more two-part hose couplings to be connected to the equipment unit, where said first coupling parts are adapted for coaction with one or more hoses for evaluating different selected criteria, such as $CO_2$-content, $O_2$-content, breathing frequency and like alternatives for pressure actuation of an expiration valve.

Similarly, it will be seen in respect of an arrangement of the kind described in the introduction that a technical problem resides in enabling one or more first coupling parts of one or more readily accessible two-part electric coupling parts to be attached to said equipment unit, where said first coupling parts are adapted for coaction with one or more external electric cables which carry electric signals representative of different chosen criteria, such as the timewise presentation of ECG-values, PLET-values and BIS-values, and instantaneous values of the same or different chosen criteria, such as the HR-value, $S_pO_2$-value and BIS-value respectively.

Another technical problem resides in enabling the use of a display unit that is designed for inclusion in an arrangement and which co-acts with an equipment unit for presenting thereon timewise variations of the measurement values applicable to chosen criteria and the instantaneous values of the same or other chosen criteria, and structure these values on said display surface so that they can be readily discerned and read, said display surface presenting one or more patient related criteria during a chosen depth of anaesthesia caused by said patient infusing a volume of anaesthesia inducing pharmaceutical per unit of time.

It will also be seen that a technical problem resides in enabling the measurement values and data obtained from chosen patient related criteria to be distributed so that said values and data can be read easily on the display surface and readily modified, for instance through the medium of display-surface related fields and the orientation of said fields and/or through the medium of button or knob actuation.

Another technical problem is one of realising the significance of allowing a first wide surface area of the display surface to be adapted to show the timewise variation of a number of criteria, and a second smaller surface area adapted to show the instantaneous values, the highest and lowest values etc. of a number of criteria.

It will also be seen that a technical problem is one of realising the significance of and the advantages afforded by allowing the first surface area to be adapted to show the timewise variation of a number of criteria, by orientating a chosen number of said criteria with the time axes being mutually equal and in superimposed relationship.

A further technical problem is one of realising the significance of and the advantages afforded by allowing a second surface area to be divided into fields such that relevant criteria can be displayed in each field, for instance in an abbreviated form, and to display adjacent thereto the instantaneous value of the criteria and the alternative maximum and minimum values or calculated values thereof.

In respect of an arrangement of the kind described in the introduction and comprising an equipment unit and a display unit, still another technical problem is one of realising the advantages that are afforded when said display unit is rotatably mounted on and easily detached from the front part of the equipment unit, such as above a container that encloses anaesthesia inducing pharmaceutical and that can be actuated by the control unit of an infusion unit, and also to realise the significance of such placement.

It will also be seen that a technical problem is one of creating with the aid of simple measures conditions that enable a control circuit in the control unit for regulating the volume of anaesthesia inducing pharmaceutical supplied by unit of time to be actuated through the medium of actuating means positioned adjacent to and preferably above said container.

Another technical problem is one of realising the significance of and the advantages afforded by allowing one or more control circuits in said control unit in the control unit for regulating criteria related to the lung ventilator to be actuated through the medium of actuating means located adjacent to and on one side of said container.

Another technical problem is one of realising the significance of and the advantages afforded by allowing one or more control circuits for controlled regulation of other criteria to be actuated through the medium of actuating means positioned in one or more rows within a third surface area of a display surface.

Another technical problem resides in creating conditions for providing within the limited volume of the equipment unit activatable regulating devices that are adapted to hold a chosen value of a chosen criterion constant for regulating purposes.

In addition to these problems it will be seen that a further technical problem resides in creating with the aid of simple measures an arrangement for total intravenous anaesthesia, where said arrangement can be managed much more simply than earlier known combined and co-ordinated arrangement set-ups and which is designed to fulfil requirements laid down by the authorities, which results in reduced maintenance costs, which is more reliable in operation, and which satisfies the desire for less or small bulk, and which is therewith mobile.

Another technical problem is one of realising the significance of and the advantages afforded by enabling the expiration gas of the patient to be conducted out into the room while the patient is anaesthetised, therewith facilitating cleaning of the ventilator and reducing the wear and tear thereon, while utilising a much smaller compressible volume (less than half).

The use of a display unit enables different magnitudes to be combined on the display surface and to phase shift and time-adapt the magnitudes, such as a pressure curve against a sample $CO_2$-curve.

It is also possible to plot one magnitude against another, for instance in an XY-diagram (PQ-loops and PV-loops).

It is also possible to establish co-variations, for instance changes in blood pressure or BIS in respect of a changed infusion rate, via a TREND-function.

A further technical problem resides in the creation of conditions with the aid of simple measures and with the use of a computer unit which enable advanced calculations or computations to be carried out by collecting together all parameters, for instance lung mechanics and indirect calorimetry and other associated advanced expert systems, where the computer is able to monitor a plurality of parameters and to draw logical conclusions therefrom, for instance give an early indication of problems and/or initiate the need for advice, for instance in reducing lung compliance (the stretchability of the lung).

Another technical problem resides in creating with the aid of simple measures and with the use of a computer unit conditions that make possible a closed-loop anaesthesia process, e.g. enable the infusion rate from which the BIS-values are obtained to be controlled, or to control the lung ventilator on the basis of the $CO_2$-values obtained.

Another technical problem is one of creating with the aid of simple measures and with the use of a computer unit conditions for reducing and/or totally eliminating mischievous alarms (several alarms resulting from the same basic cause) and to make possible so-called smart alarms, wherewith the computer unit initially sets the alarm limits on the basis of obtained patient criteria, therewith making things easier for the user.

Another technical problem is one of creating with the aid of simple measures and with the use of a computer unit conditions which enable a display image or display surface to be transmitted to another locality via telecommunications, e.g. via the Internet.

This enables the display surface to be presented on-line for consultation with another doctor in another district and locality.

The invention also provides the option of presenting display images of differing advanced degrees and therewith adapt the system to the needs and experience of the user.

The interface can also be readily updated for different languages and/or to provide technical services and updating of software in the system over the telecommunications network.

A technical problem resides in creating with the aid of simple measures and with the use of a PC-compatible computer unit conditions for advanced statistic data processing, and economic follow-up of the use of the machine and the consumption of pharmaceuticals for instance, and enables the use of standard PC-components, for instance card readers, for entering patient journals, and to utilise readily the speed and inexpensive development of PC-technology in other respects.

A further technical problem is one of creating with the aid of simple measures and with the use of a computer unit conditions for plotting the infusion characteristic of the infusion unit on the display surface and also to allow the user to insert the value mg/kg/h instead of ml/h.

Solution

The present invention thus takes at its starting point an arrangement for anaesthetising a living creature by administering thereto an infused volume of an anaesthesia inducing pharmaceutical in liquid phase per unit of time, while using one or more lung ventilator units and one or more infusion units, and by using first means to monitor unit-related criteria and second means to monitor patient related criteria.

With the intention of solving one or more of the aforesaid technical problems it is proposed in accordance with the invention that selected parts of the lung ventilator unit, with the exception of insufflation hose, expiration valve, measuring probe and a number of hoses, and selected parts of the infusion unit, with the exception of cannula and hose, are combined to form a single equipment unit, that certain of said equipment unit parts are mutually coordinated with respect to communication via a computer unit included in the equipment unit, and that said computer unit is adapted to monitor unit-related criteria and patient-related criteria.

According to proposed embodiments that lie within the scope of the present invention it is proposed that the computer unit is adapted to distinguish between therapeutic criteria and diagnostic criteria through the medium of therapeutic units and diagnostic units included in the equipment unit.

It is also proposed that one or more therapeutic units and/or one or more diagnostic units are structured on a printed circuit board or card and that, when applicable, function units are mounted on said board, and also that a plurality of such boards are coordinated in the equipment unit, and that an input of respective units is coupled internally of the equipment unit to one part of a two-part coupling device where said parts are attached to and coordinated in the equipment unit.

The coupling parts belonging to the equipment unit are comprised of one or more hose couplings and one or more electric connectors.

It is also proposed that an external hose part coupled to the lung ventilator unit and that a number of other external hose parts are arranged in a hose bundle or hose assembly that includes a hose part for insufflation gas, a hose part for controlling a patient-proximal expiration valve, two hose parts for measuring pressure difference, a pressure measuring hose part and/or a gas sampling hose part.

It is also proposed that the infusion unit will include a container or vessel that can be held firmly to the equipment unit but readily removed therefrom, said container containing an anaesthesia inducing pharmaceutical in liquid phase.

It is also proposed that the coupling parts of the equipment unit shall be connectable to a measuring probe, sensor or the like separate from the equipment unit, through the medium of an external hose part or an external electric conductor, wherewith said measuring probe, sensor or the like may include electronic circuits adapted for sensing/detecting the presence and the value of patient related criteria.

It is particularly proposed that a display unit is coupled to and/or secured to said equipment unit, and that said display unit is adapted to show the instantaneous values of one or more criteria and/or the timewise variation of said criteria on a display surface.

With the intention of solving one or more of the aforesaid technical problems it is also proposed in accordance with the invention that one or more first criteria related to one or more diagnostic units, and that one or more second criteria related to one or more therapeutic units can be presented on the display surface of a display unit, that one or more of said first criteria is/are chosen for display on the display surface as instantaneous values, and that one or more of said first criteria is/are chosen for display on said display surface as the timewise variation of the criterion.

By way of proposed embodiments that lie within the scope of the present invention it is also suggested that one or more of said second criteria is/are selected for display on the display surface as instantaneous values, and that one or more of said second criteria is/are selected for display on said display surface as timewise variation of the criterion.

In the case of certain criteria that are selected for display as the timewise variation of the criterion, the time axes are coordinated and disposed in superimposed relationship.

It is necessary for sensor associated signals to be delayed in respect of some criteria.

It is also proposed that the instantaneous values of one or more criteria related to one or more diagnostic units and/or the instantaneous values of one or more criteria related to one or more therapeutical units can be stored in the memory of the computer and presented as timewise variations of the criterion, as required.

It is also proposed that a few selected instantaneous values are stored in the memory time-related for presented time curves, so that the trend taken by the curve or certain variations in a time compressed form can be repeated.

It is also proposed in accordance with the present invention that an equipment unit will include a lung ventilator and its associated control unit, and an infusion unit and its associated control unit, and that said equipment unit is also adapted to include and detachably hold a container or vessel that encloses an anaesthesia inducing pharmaceutical in liquid phase, and that said equipment unit is also adapted to include or to co-act with said display unit.

It is also proposed that a first coupling part of a two-part hose coupling is attached to the equipment unit, and then particularly to one end-wall part thereof, said coupling part being adapted for coaction with a hose part that functions to conduct a gas flow generated in the ventilator and intended for insulation.

It is also proposed that one or more first coupling parts or one or more two-part hose couplings is/are attached to the equipment unit, and then particularly to one end-wall part thereof, said coupling part being adapted for coaction with one or more hoses for measuring pressure, measuring flow and/or analyzing gas, wherewith the equipment unit is associated with means for evaluating different criteria, such as $CO_2$-content, $O_2$-content, breathing frequency and similar criteria.

It is also proposed that one or more first coupling parts of one or more two-part electric connectors is/are connected to the equipment unit, particularly to one end-wall part thereof, wherein said connector parts are adapted for coaction with one or more external electric cables that carry sensor-related electric signals representative of different criteria, such as ECG-values, $SpO_2$-values, BIS-values, PLET-values.

It is also proposed in accordance with the invention that there is included a display unit whose display surface is divided so that there can be presented on one section of said surface one or more criteria relating to an anaesthetised patient, where the anaesthetised state of said patient has been caused by infusion of a volume of anaesthesia inducing pharmaceutical per unit of time, wherein it is particularly proposed in accordance with the invention that a first surface area of said display surface shall be adapted to display the timewise variation of a number of criteria, and that a second surface area of said display surface shall be adapted to display the instantaneous values of a number of criteria.

It is also proposed in accordance with the invention that a first surface area of said display unit shall be adapted to display the timewise variation of a number of criteria by arranging at least some of the time axes equally and in superimposed relationship.

In addition, it is proposed that a second surface area shall be divided into fields and that one or more criterion, suitably in an abbreviated form, and the instantaneous value of respective criterion can be displayed within each field.

In the case of an arrangement that includes an equipment unit and a display unit it is proposed that the display unit is rotatably mounted on and readily removable from the front part of the equipment unit, above a container that encloses anaesthesia inducing pharmaceutical and that is activatable by the control unit of the infusion unit.

It is also proposed that the control unit will include a control circuit for regulating the volume of anaesthesia inducing pharmaceutical administered per unit of time that can be activated by activating means, preferably positioned adjacent to and above said container.

It is also proposed that control circuits in the control unit for regulating criteria related to the lung ventilator can be actuated via activating means, preferably positioned adjacent to and on one side of said container.

Control circuits in a control unit for regulating a number of criteria can also be actuated via activating means that are preferably orientated in row within a third surface area of said display.

It is also proposed that the equipment will include activatable control means adapted to hold a value of a selected criterion constant.

Advantages

Those advantages primarily afforded by an arrangement for anaesthetising a living creature or patient by administering to the patient an infused volume of anaesthesia inducing pharmaceutical in liquid phase per unit of time, and while using, inter alia, a lung ventilator and an infusion unit together with associated control units, reside in the creation of conditions which enable the requisite circuits to be combined into a single equipment unit that can be easily transported and that requires little space, wherewith the requisite sensors, measuring probes, etc. to be coupled to the equipment unit can be connected readily and positively between patient and equipment unit.

The invention also includes a display unit which provides conditions for monitoring all relevant criteria in a total intravenous anaesthesia-induced state in a simple and safe fashion, so that established relative criteria and their timewise variation or instantaneous values can be overseen during surgery.

It is also possible with the aid of computer associated circuits to create conditions in which the evaluated measurement values are delayed so as to co-ordinate their appearance with respect to time.

The criteria-related measurement values can be held constant (closed loop) via computer related circuits, expert systems can be co-ordinated over telecommunications networks, and conditions can be created for distance use, relevant alarm functions can be coordinated, and different alarm criteria can be given different priorities.

The primary characteristic features of an inventive arrangement, in accordance with the present invention, are set forth in the characterizing clause of the accompanying claim 1.

The primary characteristic features of a display unit according to the present invention are set forth in the characterizing clause of the accompanying claim 21.

BRIEF DESCRIPTION OF THE DRAWINGS

An earlier known arrangement and two inventive arrangements for anaesthetising a living creature or patient by administering thereto an infused volume of anaesthesia inducing pharmaceutical in liquid phase per unit of time will now be described in more detail with reference to the accompanying drawings, in which FIG. 1 lists a number of known unit-related and patient-related criteria that can be utilised and/or evaluated beneficially with the patient in an anaesthetised state, through the medium of one or more therapeutic units and one or more diagnostic units.

DESCRIPTION OF KNOWN EMBODIMENTS

FIG. 1 lists a number of pieces of equipment, units and electric/electronic circuits required to anaesthetise a living creature or a patient by administering an infused volume of anaesthesia inducing pharmaceutical per unit of time and keeping the patient anaesthetised during surgery, and thereafter to arouse the patient from said anaesthetised state.

FIG. 1 is intended to illustrate a number of therapeutic units adapted to control the well-being of the patient, and a number of diagnostic units adapted to sense/detect and evaluate patient-related criteria for visually and/or audibly informing the anaesthetist and/or surgeon as to the state of the patient, and to provide the possibility of regulating current values for each chosen criterion.

Thus, the reference A in FIG. 1 identifies a lung ventilator. Lung ventilators of this particular kind are complicated and are known to the art and, in the following text, are simplified to comprise principally a drive unit 1A and a control unit 2A.

The lung ventilator A includes a first hose 3A adapted for delivery of insufflation gas to a patient V, and an insufflation valve 5A which is connected to the ventilator A by the hose 3A.

The lung ventilator A also includes a second hose 4A for expiration of gas from the patient V, and an expiration valve 6A connected to the hose 4A, said second hose 4A having the same cross-section as the hose 3A.

The mutually opposite ends of the hoses 3A and 4A are combined in a patient-adapted mouthpiece.

The reference B identifies a schematically illustrated and known infusion unit, where movement of an infusion syringe is effected by a part 1B and a control unit 2B.

A unit B of this kind is known to the art and is based on a container in the form of a syringe 3B that encloses an anaesthesia inducing pharmaceutical in liquid phase, and which an actuator means of a stepping motor functions to press a plunger into the syringe, wherewith pharmaceutical can pass through a hose 4B so as to create infusion of pharmaceutical into the patient's bloodstream. The control circuit 2B is designed to increase or decrease the volume infused per unit of time in a regulating fashion.

The distal end of the hose 4B is connected to a cannula 5B inserted in the patient's bloodstream.

C identifies a unit which senses the air pressure prevailing in the mouth and lungs of the patient, and includes an actuator part 1C and a control unit 2C. The instantaneous pressure in the mouth or oral cavity of the patient can be detected and determined through the medium of a hose 3C connected to the patient's mouth. This also enables the PEEP-pressure (J) to be evaluated, this pressure denoting the air pressure between insufflation phases.

D identifies a unit which includes a sensing unit 1D and a control unit 2D and which functions to evaluate the flow of gas (air) into the patient's lungs and, when necessary, the flow of expiration gas.

The unit 1D is connected to a sensor or measuring probe 5D by means of two hoses 3D and 4D, and the sensor or measuring probe 5D is designed to initiate measurement of the flow, through the medium of pressure differences P1 and P2 in the hoses 3D and 4D. As a result of time-related integration in the control unit 2D, the sensor or measuring probe is also able to establish the volume during an insufflation and expiration phase respectively in addition to establishing said flow.

The measuring probe 5D may be of the kind described and illustrated in more detail i U.S. Pat. No. 5,088,332.

The reference letter E in FIG. 1 identifies a unit which establishes the $CO_2$-content and $O_2$-content of the insulation gas and/or the expiration gas, said unit including a sensing/detecting unit 1E and an evaluating unit 2E. A hose 3E is connected to the unit 1E. The evaluating unit 2E includes circuits that enable the instantaneous value of the $CO_2$-content and/or the $O_2$-content to be established and/or the timewise variation in the pulsating insufflation or expiration gas.

F identifies a unit for establishing the patient's ECG-values and for evaluating the timewise variation of these values with the aid of a sensing unit 1F and an evaluating unit 2F.

One or more measuring points or pads are applied to the patient and connected by an electric conductor 3F, wherewith electric signals are detected and evaluated partially in the unit 1F.

G identifies a blood pressure evaluating unit that includes a sensing unit 1G and an evaluating unit 2G. More particularly, the unit evaluates an NIBP-value (Non Invasive Blood Pressure), by observing pressure variations in the hose 3G.

H identifies a unit that evaluates blood oxygen saturation, in which significant electric signals carried on a conductor 3H are received in a sensing unit 1H and evaluated in an evaluating unit 2H. This value is designated $SpO_2$. The same unit can be also used to evaluate a PLET-value.

The letter I identifies the process of evaluating the degree of consciousness or the depth of anaesthesia of a patient through the medium of a unit that includes a receiver circuit 1I and a control circuit 2I and which functions to evaluate the instantaneous brain activity of a patient.

Electric signals representing the instantaneous brain activity of the patient arrive on the conductor 3I and are received in a circuit 1I and processed in the evaluating unit 2I so as to be able to show timewise variation of the degree of consciousness and therewith enable the depth of anaesthesia of the patient to be evaluated.

The letter J identifies a device for establishing the lowest air value in respect of lung overpressure. This value can be determined under C.

Figure 2:
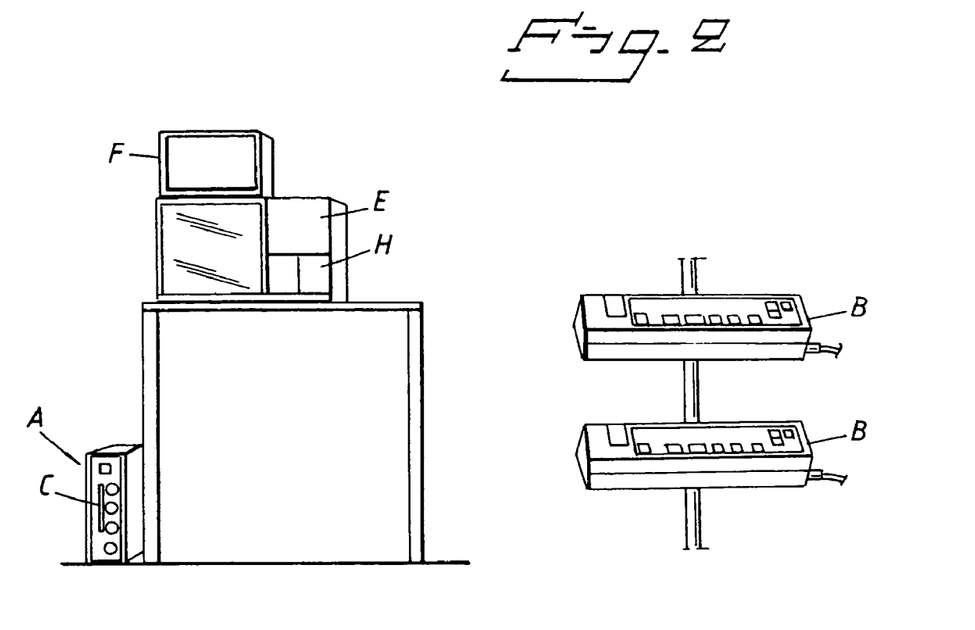
FIG. 2 is a perspective view of an earlier known system in which various therapeutic units and various diagnostic units are disposed in a room in mutually spaced relationship.

FIG. 2 is a perspective view of an earlier known array of apparatus for achieving total intravenous anaesthesia, where the individual apparatus or pieces of equipment have been combined and placed in an operating theatre in a co-ordinated manner.

FIG. 2 shows only some of the units and criteria shown in FIG. 1, these units and criteria having been given the same reference signs for the sake of illustration.

Each of the aforesaid evaluating units is designed to generate and alarm when the evaluated measurement value falls below or exceeds a predetermined limit of value.

DESCRIPTION OF EMBODIMENTS AT PRESENT PREFERRED

Figure 3:
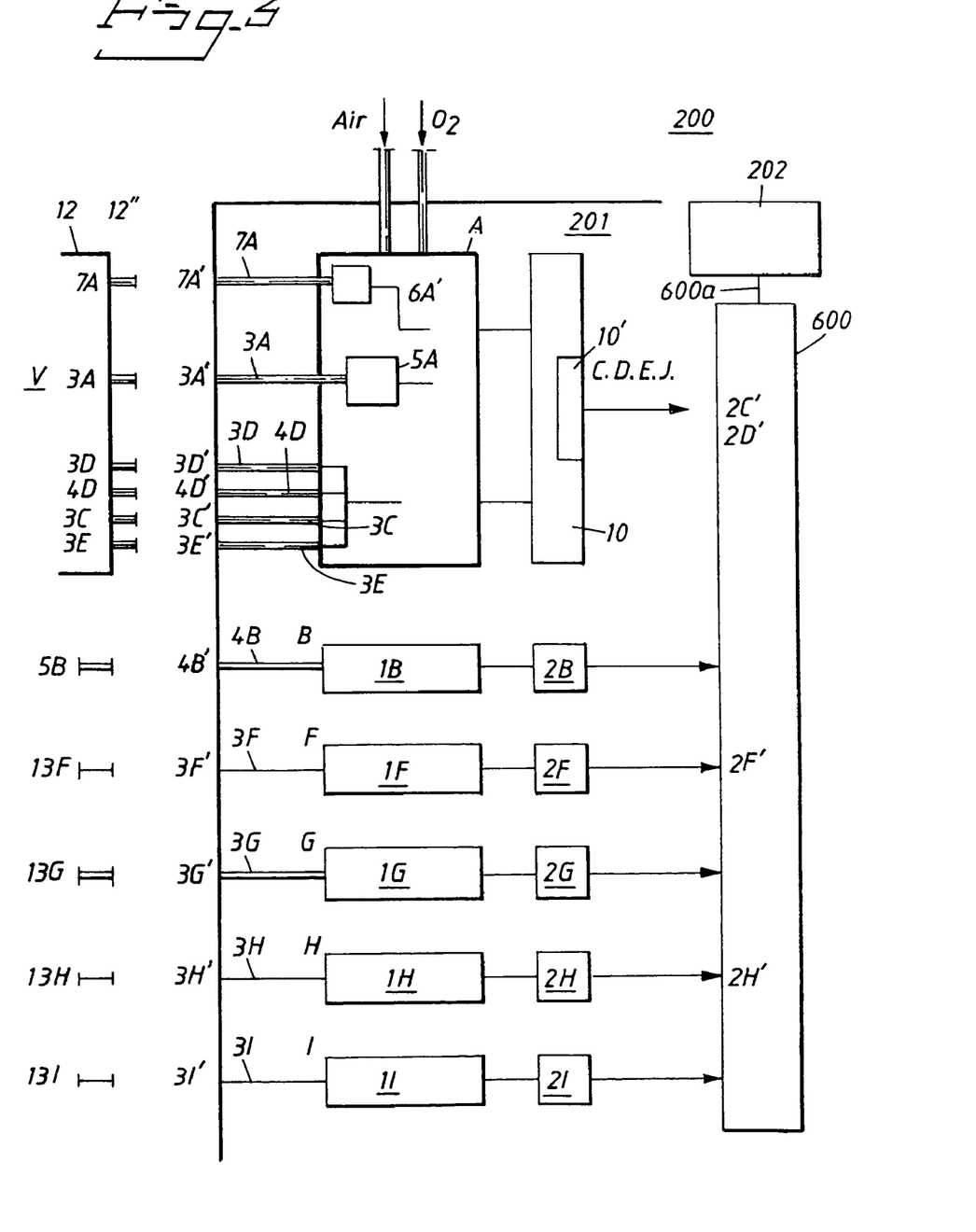
FIG. 3 is a block diagram illustrating a first embodiment of an integrated equipment unit according to the invention.
Figure 4:
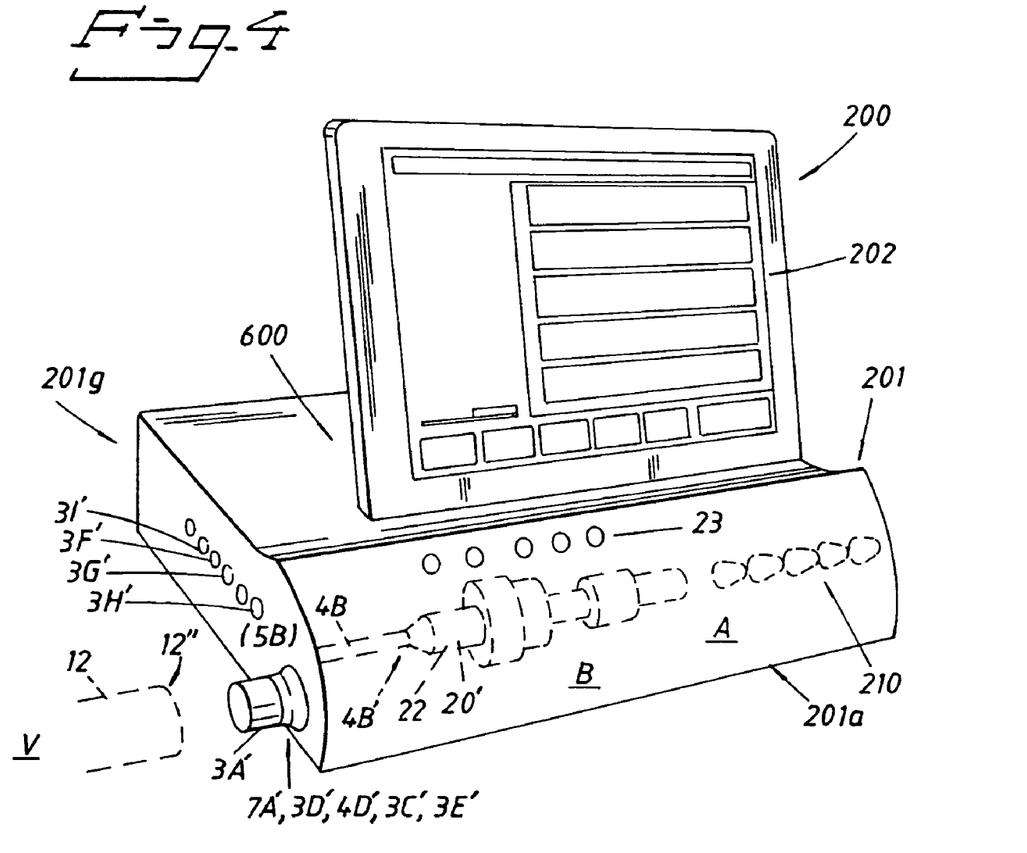
FIG. 4 is a perspective external view of an equipment unit and associated display unit included in the inventive arrangement.
Figure 5:
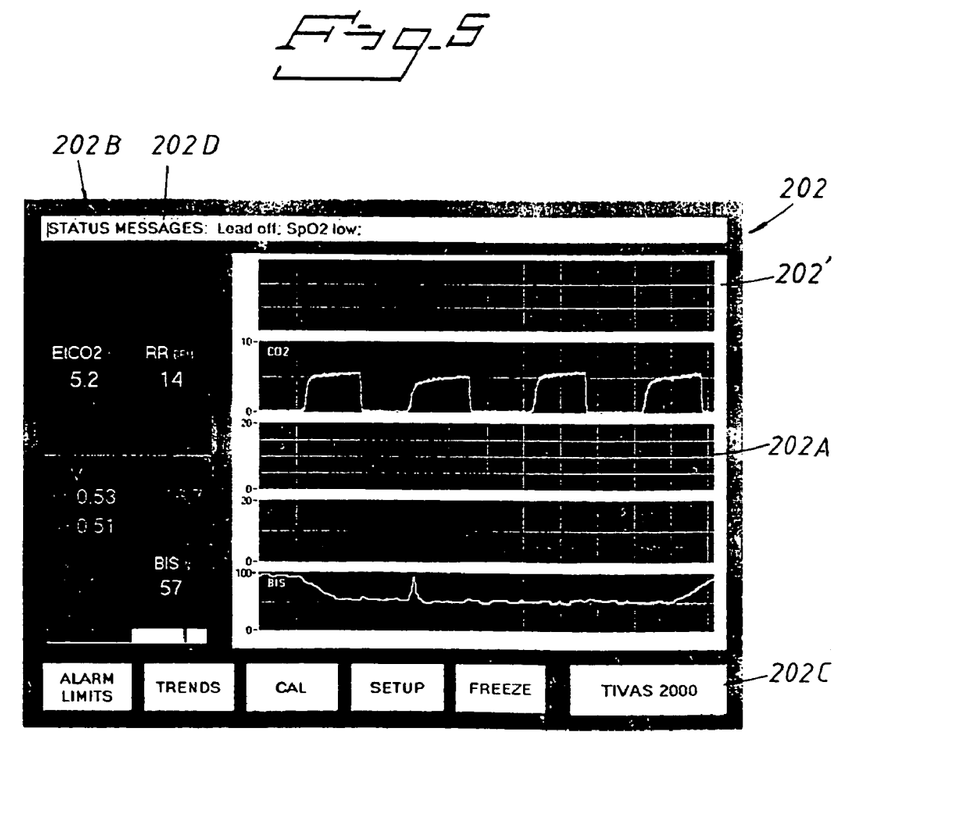
FIG. 5 is a plan view of the display surface of a display unit and shows proposed orientation of first, second, third and fourth surface areas such that timewise variation of criteria and a number of instantaneous values of said criteria can be monitored graphically and in a time relationship.

FIG. 3 is a block diagram illustrating schematically an arrangement 200 constructed and integrated in accordance with the principles of the invention, said arrangement including an equipment unit 201 (shown more clearly in FIG. 4) which comprises mutually connected necessary pieces of equipment such as to create a mobile unit to which there is connected a display unit 202 having a display surface according to FIG. 5.

The timewise variations of the values and the criteria to be evaluated and presented on the display surface 202' of the display unit 202 are in accordance with the criteria shown in FIGS. 3, 4 and 5 (within parenthesis);

(F) the timewise variation of ECG-values;
(E) the timewise variation of the $CO_2$-values (or possibly the $O_2$-values);
(H) the timewise variation of the PLET-values with respect to pulsation and strength of heart beats;
(C) the timewise variation of the air path pressure P (or the flow rate Q); and
(I) the timewise variation of the depth of anaesthesia (BIS) of the patient.

The time axes wander from left to right for all criteria.

A time axis of 20 seconds is proposed in the illustrated case. On the other hand, a time axis of about 2 hours is chosen for the BIS-curve.

The time axis of the BIS-curve can be changed so as to compress the time axis in respect of times that are longer than the maximum given time of 2 hours, so that all measurement values will be visible during the entire operation (surgical).

With the respect to the values and criteria of instantaneous values, the display surface 202' of the display unit 202 in FIG. 5 shall be divided so as to enable the following values to be determined from said criterion (in parenthesis):

(G) the NIBP-value (mmHG) with respect to the systolic blood pressure, a mean value and the diastolic blood pressure;
(F) the HR-value (BPM) denotes the heart frequency;
(E) the $EtCO_2$-value denotes the $CO_2$-value in percentage at the end of each expiration phase;
(E) the RR-value (BPM) denotes the breathing frequency calculated from the $EtCO_2$-value;
(H) the $SpO_2$-value denotes in percentage the blood oxygen saturation value;
(E) the $FiO_2$-value denotes the fraction of inspired oxygen content in the insufflation gas and possibly also in the expiration gas ($FeO_2$);
(D) the VL-value (liters) denotes the volume of insufflated gas and the volume of expired gas;
(C) the P-value (cm $H_2O$) denotes the pressure of the respiratory tract and PEEP-value (J), disclosing the pressure between two insufflation phases;
(B) the V-inf. value (ml) denotes the volume of anaesthesia inducing pharmaceutical delivered to the patient;
(B) the P occl-value denotes the pressure in the container for the infusion unit, in the form of a bar graph; and
(I) the BIS-value denotes the depth of anaesthesia or the degree of consciousness of the patient in percent.

In the case of the present application it is necessary to force insufflation gas periodically to the patient V through an insufflation hose 3A, whereas expiration gas is allowed to pass directly to the surroundings. This can be effected through the medium of a pressure-actuated valve 15. It shall be possible to move the valve 15 to a closed state via a limited overpressure on a line 7A.

Such an arrangement, without hose (4A) for the expiration gas, provides a significantly smaller compressible volume, smaller than half the volume that needs to be actuated by the lung ventilator.

FIGS. 3 and 4 illustrate an equipment unit 201 that includes a lung ventilator A and a number of requisite connection hoses, among other things.

As will be seen from FIG. 3, the ventilator A has an air intake and a gas ($O_2$) intake, and the insufflation gas through the hose 3A may consist of pure air, pure $O_2$-gas or a chosen mixture thereof.

The hose 3A is thus adapted for insufflation gas and is connected to a valve 15.

The hose 3A and all other hoses and electric conductors have been identified with the same reference signs along their full length.

It will be noted, however, that all hoses and conductors/lines will normally have within the equipment unit 201 an internal hose or conductor section that is connected to a two-part coupling unit in one end-wall of the equipment unit, and will include an external hose or conductor section that is connected to a valve, measuring probe or the like.

FIG. 3 also shows the known valve (6A in FIG. 1) divided functionally so that a part 6A' is included in the ventilator A and functions to apply an overpressure in the hose 7A. This overpressure can be varied between two values and in accordance with the phase of the insufflation gas.

The other part is comprised of the valve 15.

The hose 7A is designed to control the valve 15 from one state to another state with the aid of the valve 6A' and with a controlled overpressure, so as to force insufflation gas into the patient V in one first valve position and to enable expiration gas to pass freely in a second valve position.

This free passage of the expiration gas can take place against an adapted counterpressure (the PEEP-pressure) which may range from 2–20 cm water column for instance.

The hoses 3A and 4D are pressure-measuring hoses for measuring pressure differences and pressure variations generated by a gas flow.

The hose 3C is solely for measuring pressure.

The hose 3E is intended to conduct insufflation gas or expiration gas to an evaluating unit for gas analysis.

The four hoses 3C, 3E, 3D and 4D are together connected to equipment 10 for sensing and evaluating the criteria C, D, E and J. The values obtained are sent to a computer unit 600.

The equipment intended for criteria B, F, G, H and I is also integrated in the equipment unit 201, with their respective evaluating units 2B, 2F, 2G, 2H and 2I connected to the computer unit 600.

It will be evident from this that the equipment unit 201 shall have connected thereto seven external air or gas conducting hose parts or sections 7A, 3A, 3D, 4D, 3C, 3E and 3G, preferably of mutually different cross-sections and/or different orientation, and also an external hose 4B for conducting anaesthesia inducing pharmaceutical, and three external electrical connecting lines 3F, 3H and 3I.

Also connected to the computer unit 600 is a display unit 202, which will be described in more detail below with reference to FIGS. 5 and 8.

FIG. 4 illustrates in perspective an inventive arrangement 200 that includes an equipment unit 201 and associated display unit 202, for anaesthetising a living creature by administering thereto an infused volume of anaesthesia-inducing pharmaceutical per unit of time with the aid, inter alia, of a lung ventilator and an infusion unit with associated control units for regulating the magnitude of the gas volume or the gas volume and/or the volume of pharmaceutical per unit of time as necessary.

The complete arrangement 200 comprises and/or includes a plurality of external sensors, measuring probes and the like and requisite external hoses or conductor sections in addition to the compact equipment unit 201 and associated display unit 202.

Not all of these sensors and measuring probes are shown, but merely indicated.

An external hose section or an external electrical conductor section shall be capable of detachably connecting respective sensors and measuring probes to the equipment unit 201.

Thus, there is shown in FIGS. 3 and 4 a number of sensors which are coordinated via an external electrical conductor section or via an individual external hose section and each connected via an individual two-part coupling device to a respective connecting part in the end wall 201G of the equipment unit 201. The sensor 13F is connected to the connector part 3F' via an external conductor section.

Pressurised air is delivered to a cuff-like sensor 13G via an external section of the hose 3G and the cuff squeezed or tightened so as to stop the flow of blood. As the pressure of the air is slowly released, the pulsations occurring in the pressurised air are sensed as the blood is again allowed to flow freely.

This section of the hose 3G between the cuff and the equipment unit 201 is connected to a connector part 3G' in the end wall 201g via a two-part connector.

A sensor 13H is connected to a connector 3H' in the end wall 201g via an external electrical conductor section and via a two-part connector, for evaluating the $S_pO_2$-value.

A sensor 13I is connected to a connector 3I' in the end wall 201g via a two-part connector and via an external electrical conductor section, for evaluating the BIS-values.

These sensors 13F, 13G, 13H and 13I may be of a known kind.

The external sections of the hoses 3A, 3C, 3D, 4D, 3E and 7A are all coupled to a mouth-proximal valve arrangement that includes a valve 15 and a measuring probe 42.

The equipment unit 201 is also designed to include and enclose essential parts of a lung ventilating unit A whose internal hose section for the insufflation hose 3A opens out into a two-part hose coupling that has a connection part 3A' in the end-wall 201g.

Correspondingly, the internal sections of the hoses 7A, 3D, 4D, 3E and 3C are adapted to open out into a respective two-part hose coupling that includes a connector part 7A', 3D', 4D', 3E' and 3C' located in the end-wall 201g.

The invention also allows all or at least selected external sections of all hoses to the valve 15 and the measuring probe 42 to be collected in a single hose bundle 12, with a connecting part 12" adapted for all hose section adapted for fixed but readily removed coaction with the connector parts 7A', 3A', 3D', 4D', 3E' and 3C' in the end-wall part 201g.

The equipment unit 201 is also adapted to include essential parts of said infusion unit B, including the control unit 2B and the actuator part 1B.

The equipment unit 201 is also designed to include and detachably hold a container or vessel 20' belonging to an infusion unit B and containing anaesthesia inducing pharmaceutical 22 in liquid phase, and is also designed to carry said display unit 202.

As before mentioned, there extends between the valve 14 and measuring probe 42 and the equipment unit 201 a hose bundle 12 which includes a plurality of external sections of the hoses used.

Figure 7:
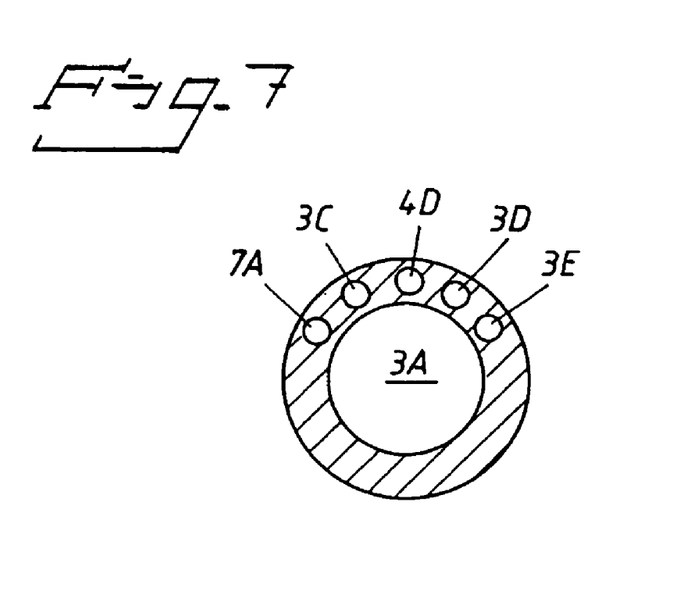
FIG. 7 illustrates an example of a hose bundle with a hose cross-section that can be used as an integrated connection between the equipment unit and the valve/measuring probe shown in FIG. 6.

FIG. 7 shows a proposed cross-section of one such hose bundle 12, from which it will be evident that solely external hose sections for hoses 3A, 3D, 4D, 3C, 3E and 7A are co-ordinated in an exemplifying manner, whereas the hoses 4B and 3G have individual hose coupling 4B', 3G' at the side of the hose coupling common to remaining hoses and including the connecting part or coupling device 12".

As will be seen from FIG. 4, there is attached to one end-wall part 201g of the equipment unit 201 a first coupling part of the two-part hose coupling, where it is indicated that one connecting part 3A' is placed centrally and where the connecting parts 7A', 3D', 4D', 3E' and 3C' are orientated peripherally for coaction with an external hose bundle 12 of given cross-section according to FIG. 7.

Anaesthesia inducing pharmaceutical is administered under an adapted pressure via the coupling part 4B', and the NIBP-values are sensed via the coupling part 3G'.

Also mounted on the same end-wall part 201g of the equipment unit 201 are one or more connector parts of one or more electrical connectors, said connector parts being adapted for coaction with one or more external electric cables or conductors that carry electric signals representative of different criteria, such as ECG-values (3F'), $S_pO_2$-values and PLET-values (3H') and BIS-values 3I' respectively.

FIG. 5 illustrates a proposed embodiment of a suitable display surface 202' in slightly larger scale than in FIG. 4.

The display unit 202 is adapted for co-operation with an arrangement of the kind described in the introduction and the display surface 202' functions to present one or more criteria applicable to a patient in a state of anaesthesia induced by administering to the patient a volume of anaesthesia inducing pharmaceutical per unit of time, by infusion.

Figure 8:
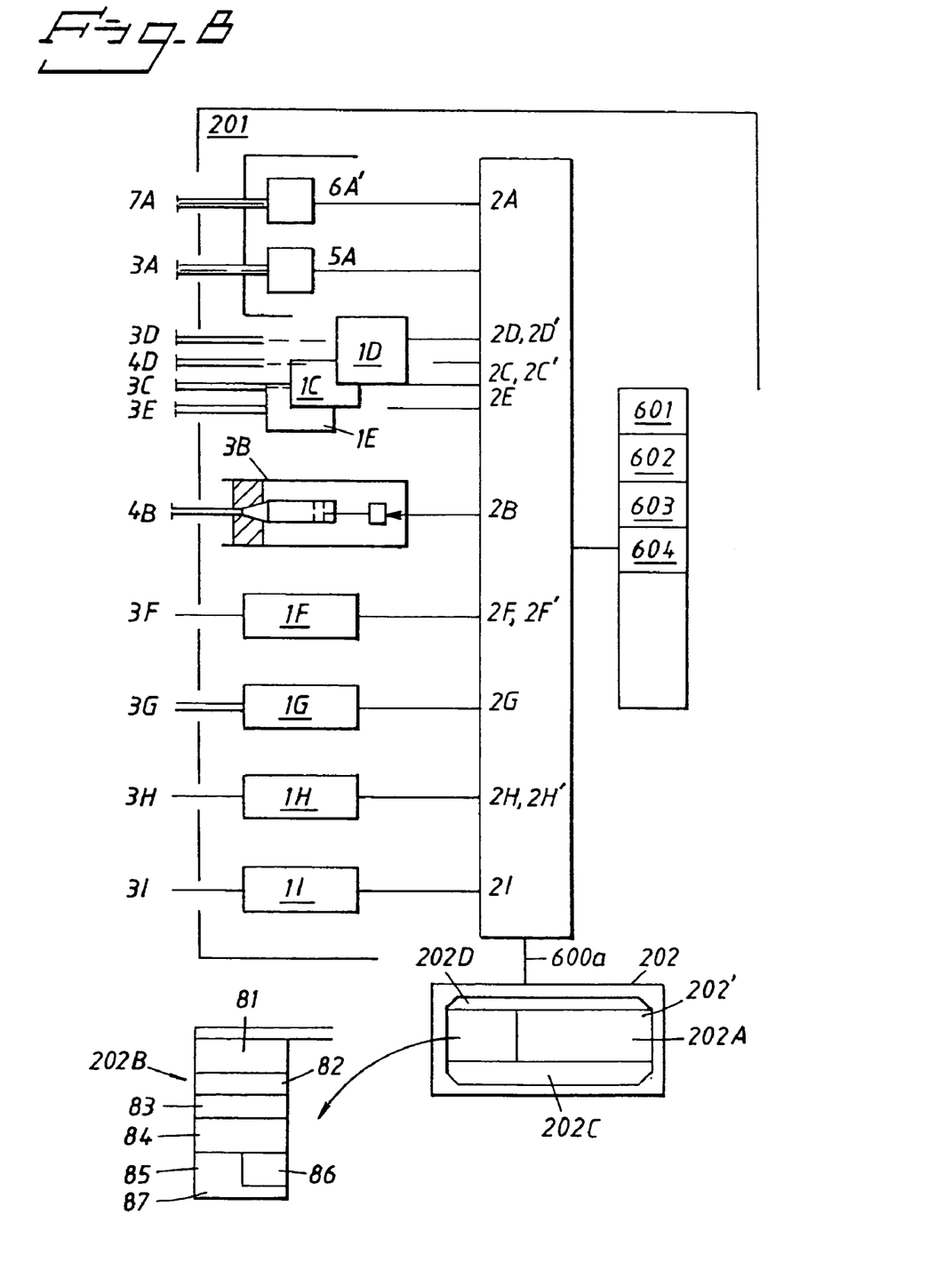
FIG. 8 is a block diagram of a second integrated equipment unit according to the invention, including a number of electric circuits, a lung ventilator and associated control unit, and an infusion unit and associated control unit for regulating the supply of anaesthesia inducing pharmaceutical, and a computer unit and connected display unit.

It will be seen from the figure, and also from FIG. 8, that the display surface 202' is divided into a number of large and small surface areas.

A first surface area 202A is adapted to show the timewise variation of a number of criteria, while a second surface area 202B is adapted to show the instantaneous values of a number of criteria.

The first surface area 202A is adapted to show the timewise variation of a chosen number of criteria, by equally orientating the time axes of a number of criteria in mutually superimposed relationship.

More specifically, four different criteria are shown with the same time axes in the following order: uppermost ECG-values, followed by $CO_2$-values, followed by PLET-values and then the P-values.

The lowermost field shows the BIS-values with an own time axis.

The second surface area 202B is divided into fields in which a criterion is shown in each field, in an abbreviated form, with the instantaneous value of respective criteria shown adjacent thereto.

FIGS. 5 and 8 illustrate in all desirable clarity that an uppermost field 81 discloses the NIBP-value and the RR-values, the next following field 82 discloses the $EtCO_2$ and RR values, the next following field 83 discloses the $S_pO_2$-value and the $FiO_2$-value, the next following field 84 discloses VL and the P-values, and that the next following field 85 discloses the value Vinf concerning the volume of applied anaesthesia inducing pharmaceutical, while a field 86 shows the mean BIS-value in percent. The display also includes a field 87 for the Poccl-value, the value of the pressure in container 20'.

More particularly, it is proposed in accordance with the present invention that one or more first criteria related to one or more diagnostic units, and one or more second criteria related to one or more therapeutic units are allowed to be presented on a display unit or a display surface, that one or more of said first criteria is/are selected for display on said display surface as instantaneous values, and that one or more of said first criteria is/are selected for display on said display surface as the timewise variation of the criterion.

One or more of said second criteria are chosen for display on the display surface as instantaneous values, and one or more of said second criteria are chosen for display on said display surface as the timewise variation of the criterion.

In the case of some criteria chosen for display as the timewise variation of the criterion, the time axes are co-ordinated and arranged in superimposed relationship.

In order to obtain concordance of the time axes and instantaneous values, it is necessary with respect to some criteria to delay sensor-related signals, for instance through the medium of time delay circuits 2C', 2D', 2F' and 2H' with mutually adapted time delays.

It is also proposed that the instantaneous values and/or graph-related values of one or more criteria related to one or more diagnostic units, and/or corresponding values of one or more criteria related to one or more therapeutic units are stored in the computer memory so that the instantaneous values can be shown as timewise variation of the criterion and the graph-related values shown as compressed trends when necessary.

Referring back to FIG. 4, it will be seen that the display unit 202 is rotatably mounted on and readily removed from the front part 201a of the equipment unit 201 and above a container 20' that contains anaesthesia inducing pharmaceutical 22 and which can be actuated by the control circuit of the infusion unit.

A control unit for regulating the volume of anaesthesia inducing pharmaceutical administered per unit of time can be actuated through the medium of an activating device positioned adjacent to and above the container.

One or more control circuits for regulating other criteria, such as criteria relating to the lung ventilator, can be actuated via activating means positioned adjacent to and on one side of said container 20', these activating means being referenced 210.

It is also possible within the scope of the invention to allow one or more control circuits included in the control unit for regulating chosen criteria to be actuated through the medium of activating means orientated in one or more rows, such as within a third surface area of the display unit referenced 202C in FIG. 4.

The equipment unit 201 also includes regulating means which are activated via the computer unit and which function to regulate a value of a chosen criterion and/or keep said value constant.

Figure 6:
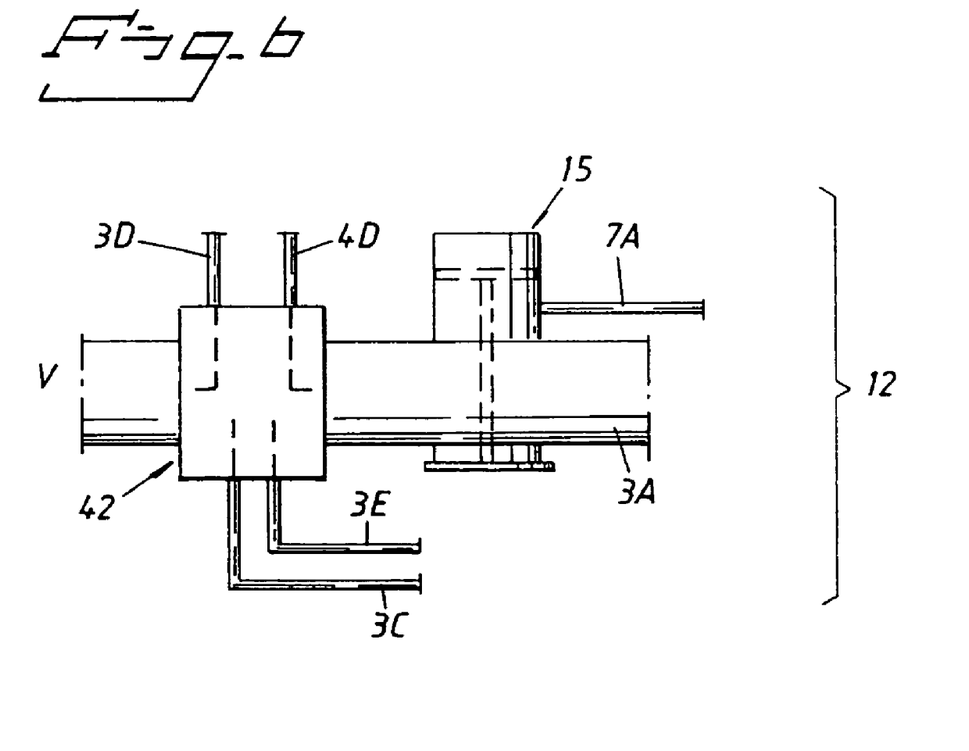
FIG. 6 illustrated the principle connection of a measuring probe and a valve for enabling the flow and volume of insufflation gas and expiration gas to be determined and controlled, and also other criteria related to said gas.

FIG. 6 shows schematically a valve arrangement 15 and an adjacent measuring probe 42 for controlling lung ventilation and for measuring different criteria relating to the administered insufflation gas, and when necessary also criteria relating to the expiration gas.

FIG. 7 is a cross-sectional view of an external hose bundle 12 whose one end is able to co-act with the equipment 12 via a coupling device 12", while the other end of said hose bundle 12 is adapted for coaction with the valve 15 and the measuring probe 42.

For instance, it will be seen from FIG. 7 that the hose bundle 12 has a large hose cross-section for the connection 3A' and the hose 3A, a hose cross-section for connection 7A' and the hose 7A, a hose cross-section for the connection 3D' and the hose 3D, a hose cross-section for the connection 4D' and the hose 4D, a hose cross-section for the connection 3E' and the hose 3E, and a hose cross-section for the connection 3C' and the hose 3C.

FIG. 8 is a schematic block diagram showing another proposed embodiment of the mutually co-acting parts and circuits enclosed in the equipment unit 201, wherewith certain of said parts and circuits can be controlled and monitored by a computer unit 600 that has associated programs and storage units.

This embodiment is based on the concept of co-ordinating requisite evaluating units included in utilised units to be included in a common computer unit 600. A person skilled in this art will be able to produce on the basis of the above description software and a control system adapted to the aforementioned functions, and it is therefore deemed unnecessary to describe the necessary programming to any greater extent in this document.

Where possible, the reference signs given in FIG. 3 have also been used in FIG. 8 to identify corresponding function blocks.

The lung ventilator A has also been described in connection with the circuits that require pressure and flow in order to determine desired criteria through the medium of said circuits. These have been shown and described with reference to the lung ventilator.

It should be mentioned that the majority of the function block shown in FIG. 8 for selected criteria are known to the art, and will not therefore be described in greater detail.

Thus, FIGS. 3 and 8 show that the occurrence/presence of and the value of chosen criteria are delivered to a central or common computer unit 600 which is connected to the display unit 202 via a line 600A which is adapted for two-way information, so that the computer unit 600 is able to transmit desired values to the display unit 202, while the third surface area 202C can be used to send instructions and messages to the computer unit 600 which changes the conditions of said criteria on the basis of these signals.

It is applicable to both embodiments that structuring of the instantaneous values presented on the display unit are field-related in the manner shown in the enlarged view of FIG. 5.

With regard to the surface area 202C, it can be mentioned that alarm limits can be entered and evaluated via manual actuation of the surface section -Alarm Limits- of the surface area 202C, that certain measurement values can be presented over a long time period (the time axis is extended) via the surface section -TRENDS-, calibration can be effected via -CAL-, certain measurement values can be presented via -SETUP-, and the timewise variation can be frozen for closer assessment via -FREEZE-.

The display surface 202' has a fourth surface area 202D in which other relevant information is presented, such as malfunctioning and/or an alarm.

Both of the aforedescribed embodiments incorporate different time delays for compensation of so-called lag time.

In order to achieve timewise-correct indication of several criteria it is necessary to delay rapidly evaluatable criteria so that said criteria can be displayed on the display at the same moment in time as criteria that are evaluated more slowly.

For instance, it can be assumed that the $CO_2$-value and the $O_2$-value for criterion E is the last value to appear with respect to time, and consequently it is necessary to delay other criteria over an adapted time period, so that these values will appear simultaneously in co-ordination on the display surface. In practice, the delay concerned will be shorter than one second.

Consequently, equipment corresponding to equipment 2C, 2D, 2F and 2H include adapted time delay circuits 2C', 2D', 2F' and 2H', which are preferably individually adapted.

The computer equipment 600 of both embodiments may be equipped with an -expert system-, where a utilised computer program is adapted to sense and calculate and interpret obtained measurement values and also to set alarm limits.

The computer program of the FIG. 8 embodiment is referenced 601.

A computer program 602 may be adapted to control received measurement values against set point values in a closed-loop-sequence.

Computer program 603 may be used to change the limit values for adapted criteria in accordance with the patient's weight, sex, race, etc.

The information displayed on the display surface can be transferred to another display screen with the aid of a computer program 604 and also with the aid of the telecommunications network, such as over the Internet.

Although the invention has been described with reference to the use of a sole infusion unit B, it will be understood that two or more such units can be used, with the same or mutually different pharmaceutical.

The lung ventilator A can be duplicated so that one unit is used for each individual lung, therewith enabling separate control of insufflation and expiration.

It is also proposed that therapy control is effected through the medium of keys and knobs and the equipment unit 201, while diagnostic control can be effected via the display unit 202.

The two illustrated and described embodiments of the invention are also based on the assumption that the various parts of the equipment unit are mutually co-ordinated with respect to communication via a computer unit provided in the equipment unit, and that said computer unit is adapted to monitor unit-related criteria and patient-related criteria.

The computer unit 600 is also adapted to distinguish between therapeutic criteria and diagnostic criteria through the medium of therapeutic units and diagnostic units included in said equipment unit, said therapeutic and diagnostic units being co-arranged on a printed circuit board included in the equipment unit and, when applicable, having function units mounted thereon, wherewith an input to respective units is connected internally to one part of a two-part coupling device with said part attached to the end-wall of said equipment unit.

For instance, it can be mentioned that an ECG-board or card has a construction that requires three (3) connection electrodes with each electrode having a respective external conductor section.

The $CO_2$-board and $O_2$-board has a gas analysing unit mounted thereon.

Both boards are connected to a separately mounted sampling pump.

It will be understood that the invention is not restricted to the aforedescribed and illustrated exemplifying embodiments thereof and that modifications can be made within the scope of the inventive concept as illustrated in the accompanying claims.

The invention claimed is:

1. An arrangement for anaesthetising a living creature and maintaining said creature anaesthetised, by administering to said creature an infused volume of an anaesthesia inducing pharmaceutical in liquid phase per unit of time, said arrangement comprising:
   a. at least one lung ventilator unit, an insufflation hose extending from said at least one lung ventilator unit to an expiration valve for being oriented adjacent to or mouth-proximal said creature, a measuring probe spaced from said at least one lung ventilator unit, and a plurality of further hoses extending from said at least one lung ventilator unit,
   b. at least one infusion unit having parts related to said infusion unit co-ordinated to said arrangement, a cannula, and a hose extending from said infusion unit and operatively connected to said cannula, c. first means related to a computer unit for monitoring unit-related criteria, d. second means related to said computer unit for monitoring creature-related criteria, e. a display unit exposing a display surface for said unit-related criteria and said creature-related criteria, f. said valve having a first part and a second part that each perform different functions, said first part being included in the at least one ventilator unit for applying an over pressure to one of said hoses, and said second part being moveable from a first valve member position to a second valve member position, so as to force insufflation gas into the creature when said second part is in said first valve member position and to enable expiration gas to pass freely from said creature when said second part in said second valve member position, g. said plurality of hoses extending from said at least one ventilator unit are adapted as pressure-measuring hoses for measuring pressure differences and pressure variations generated by a gas flow in said measuring probe adjacent said valve by using said insufflation gas flow, h. said plurality of hoses extending from said at least one ventilator unit further including a gas analysis hose operatively associated with said measuring probe and adapted to enable flow of at least one of insufflation gas and expiration gas to an evaluating unit for gas analysis, i. said gas analysis hose and said plurality of hoses extending from said at least one ventilator unit are connected to equipment for sensing and evaluating selected criteria, said selected criteria including a time wise variation of the at least one of air path pressure and a flow rate, a VL-value denoting the volume of insufflated gas and a volume valve of expired gas, and/or a FiO2 value denoting a fraction of inspired oxygen content in the insufflation gas and in the expiration gas, j. wherein a plurality of values obtained from said evaluating unit are sent to said computer unit, said plurality of values including:

k. a HR value denoting a heart frequency, l. a NIBP-value denoting a systolic blood pressure, a mean value and a diastolic blood pressure, and/or m. a $SpO_2$ value denoting, in percentage, a blood oxygen saturation value;

n. the plurality of values representing item "k" to "m" are each received by their respective control unit, and wherein each of said control units is connected to said computer unit, o. an information carrying line connecting said computer unit to said display unit, p. said information carrying line being adapted for a two-way information exchange so that the computer unit is able to transmit desired values to the display unit, q. whereby a selected surface area of said display unit can be used to send instructions and messages to said computer unit, and r. said computer unit being equipped with an expert system wherein a utilised computer program is adapted to sense and calculate and interpret obtained measurements values and set alarm limits.

2. An arrangement according to claim 1, further comprising an equipment unit including at least said at least one ventilator unit, at least one therapeutic unit and at least one diagnostic unit, wherein at least one of said at least one therapeutic unit and said at least one diagnostic unit is structured on at least one printed circuit board, which has a function unit mounted thereon; wherein said at least one board is co-ordinated in an equipment unit, with one input of respective units connected to one part of a two-part coupling device, and wherein said part of said coupling device is attached to and co-ordinated on said equipment unit.

3. An arrangement according to claim 2, wherein said equipment unit has connected thereto and/or affixed thereto said display unit, which is adapted for the display of at least one of instantaneous criteria value and timewise variation of the criterion on said display surface.

4. An arrangement according to claim 1, wherein first criteria related to a diagnostic unit, and second criteria related to a therapeutic unit can be presented on a display surface of the display unit; wherein said first criteria are chosen for display on said display surface as instantaneous values; and wherein said first criteria are chosen for display on said display surface as timewise variation of the criterion.

5. An arrangement according to claim 1, wherein time axes of selected criteria of at least one of said unit-related criteria and said creature-related criteria chosen to be shown as timewise variation of respective criteria are co-ordinated and arranged in mutually superimposed relationship.

6. An arrangement according to claim 1, wherein signals generated by a measuring probe, a sensor in respect of chosen criteria of said unit-related criteria or said creature-related criteria are time-delayed prior to said chosen criteria being presented on the display surface.

7. An arrangement according to claim 1, wherein instantaneous values and values concerning time related graphs for criteria related to a diagnostic unit and instantaneous value concerning time-related graphs for criteria related to a therapeutic unit can be stored in memories for presentation as timewise variation of the respective criteria.

8. An arrangement according to claim 7, wherein the timewise variation of said respective criteria can be presented in a time compressed form.

9. An arrangement according to claim 2, further comprising an equipment unit including at least said at least one lung ventilator unit and a plurality of said hoses, and wherein a first coupling part of a two-part hose coupling of at least one of said hoses is attached to said equipment unit, and said coupling part is adapted for a co-action with an external hose section for an insufflation gas flow and a plurality of external hose sections.

10. An arrangement according to claim 2, wherein at least one first coupling part of said two-part coupling device is attached to the equipment unit, and wherein said at least one first coupling part is adapted for co-action with a unit for evaluating different criteria, said different criteria including $CO_2$-content, $O_2$-content, and/or breathing frequency.

11. An arrangement according to claim 2, wherein the equipment unit has attached thereto at least one two-part electric connector, said electric connector including a first part adapted for co-action with an external electric cable that carries sensor-related electric signals representative of different criteria, said different criteria including at least ECG-values, $SpO_2$-values, BIS-values, and/or PLET-values.

12. An arrangement according to claim 1, further comprising an equipment unit including at least said at least one lung ventilator unit and a plurality of said hoses, and wherein a first coupling part of a two-part hose coupling of at least one of said hoses is attached to said equipment unit, and said coupling part is adapted for a co-action with an external hose section for an insufflation gas flow and a plurality of external hose sections.

* * * * *